(12) United States Patent
Timmins et al.

(10) Patent No.: US 11,242,503 B2
(45) Date of Patent: Feb. 8, 2022

(54) METHOD FOR DISSOCIATING CELL AGGREGATES

(71) Applicant: CENTRE FOR COMMERCIALIZATION OF REGENERATIVE MEDICINE, Toronto (CA)

(72) Inventors: Nicholas Timmins, Scarborough (CA); Lesley Chan, Cambridge, MA (US)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 401 days.

(21) Appl. No.: 16/072,379

(22) PCT Filed: Jan. 25, 2017

(86) PCT No.: PCT/CA2017/050073
§ 371 (c)(1),
(2) Date: Jul. 24, 2018

(87) PCT Pub. No.: WO2017/127921
PCT Pub. Date: Aug. 3, 2017

(65) Prior Publication Data
US 2019/0031990 A1    Jan. 31, 2019

Related U.S. Application Data

(60) Provisional application No. 62/287,103, filed on Jan. 26, 2016.

(51) Int. Cl.
| | | |
|---|---|---|
| *C12M 3/08* | (2006.01) | |
| *C12M 1/00* | (2006.01) | |
| *C12M 1/33* | (2006.01) | |
| *C12M 3/02* | (2006.01) | |
| *C12N 5/0735* | (2010.01) | |
| *C12M 1/06* | (2006.01) | |

(52) U.S. Cl.
CPC ............... *C12M 3/08* (2013.01); *C12M 3/02* (2013.01); *C12M 27/02* (2013.01); *C12M 45/02* (2013.01); *C12M 45/06* (2013.01); *C12M 45/09* (2013.01); *C12M 47/04* (2013.01); *C12N 5/0606* (2013.01); *C12N 2513/00* (2013.01); *C12N 2521/00* (2013.01)

(58) Field of Classification Search
None
See application file for complete search history.

(56) References Cited

U.S. PATENT DOCUMENTS

| | | |
|---|---|---|
| 8,008,075 B2 | 8/2011 | Green et al. |
| 8,895,300 B2 | 11/2014 | Schulz |
| 9,944,894 B2 | 4/2018 | Davis et al. |
| 2005/0221476 A1 | 10/2005 | Sen et al. |
| 2008/0187519 A1* | 8/2008 | Sen ...................... C12N 5/0623 424/93.7 |
| 2013/0344598 A1 | 12/2013 | Nistor |
| 2016/0215268 A1 | 7/2016 | Fryer et al. |

FOREIGN PATENT DOCUMENTS

| | | |
|---|---|---|
| EP | 2730649 A1 | 5/2014 |
| WO | 2009050694 A1 | 4/2009 |
| WO | 2010035136 A2 | 4/2010 |
| WO | 2014106141 A1 | 7/2014 |
| WO | 2016113369 A1 | 7/2016 |

OTHER PUBLICATIONS

Ghasemian, et al. (2020) "Hydrodynamic characterization within a spinner flask and a rotary wall vessel for stem cell culture", Biomedical Engineering Journal, 157: article 107533, 11 pages long. (Year: 2020).*
van der Loo, et al. (2012) "Scale-up and manufacturing of clinical-grade self-inactivating [gamma]-retroviral vectors by transient transfection", Gene Therapy, 19: 246-54. (Year: 2012).*
Amit, et al. (2009) "Embryonic Stem Cells: Isolation, Characterization and Culture", Advances in Biochemical Engineering/Biotechnology, vol. 114: 173-84. (Year: 2009).*
Abbasalizadeh, et al., Bioprocess Development for Mass Production of Size-Controlled Human Pluripotent Stem Cell Aggregates in Stirred Suspension Bioreactor, Tissue Engineering: Part C, 2012, 18(11):831-851.
Chen, et al., Thermoresponsive Worms for Expansion and Release of Human Embryonic Stem Cells, Biomacromolecules, 2014, 15:844-855.
Cormier, et al., Expansion of Undifferentiated Murine Embryonic Stem Cells as Aggregates in Suspension Culture Bioreactors, Tissue Engineering, 2006, 12(11):3233-3245.
Fluri, et al., Derivation, Expansion and Differentiation of Induced Pluripotent Stem Cells in Continuous Suspension Cultures, Nature Methods, 2012, 9(5):509-516.
Fok, et al., Shear-Controlled Single-Step Mouse Embryonic Stem Cell Expansion and Embryoid Body-Based Differentiation, Stem Cells, 2005, 23:1333-1342.
Gilbertson, et al., Scaled-Up Production of Mammalian Neural Precursor Cell Aggregates in Computer-Controlled Suspension Bioreactors, Biotechnology and Bioengineering, 2006, 94(4):783-792.
Haraguchi, et al., Simple Suspension Culture System of Human iPS Cells Maintaining Their Pluripotency for Cardiac Cell Sheet Engineering, Journal of Tissue Engineering and Regenerative Medicine, 2015, 9:1363-1375.
Hunt, et al., Factorial Experimental Design for the Culture of Human Embryonic Stem Cells as Aggregates in Stirred Suspension Bioreactors Reveals the Potential for Interaction Effects Between Bioprocess Parameters, Tissue Engineering: Part C, 2014, 20(1)76-89.

(Continued)

*Primary Examiner* — Robert M Kelly
(74) *Attorney, Agent, or Firm* — Quarles & Brady LLP

(57) ABSTRACT

A method for dissociating cell aggregates in an agitated reactor. The method comprises providing a cell culture comprising cell aggregates in the agitated reactor, contacting the cell aggregates with a dissociation reagent, generating a dissociation force in the agitated reactor and exposing the contacted cell aggregates to the generated dissociation force under conditions sufficient to dissociate the contacted cell aggregates. The method may be used in a process for passaging cells and/or generating dissociated differentiated cells from stem and/or progenitor cells.

27 Claims, 6 Drawing Sheets

(56) References Cited

OTHER PUBLICATIONS

Kallos, et al., Inoculation and Growth Conditions for High-Cell-Density Expansion of Mammalian Neural Stem Cells in Suspension Bioreactors, Biotechnology and Bioengineering, 1999, 63:473-483.

Kempf, et al., Cardiac Differentiation of Human Pluriopotent Stem Cells in Scalable Suspension Culture, Nature Protocols, 2015, 10(9):1345-1361.

King, et al., Bioreactor Development for Stem Cell Expansion and Controlled Differentiation, Current Opinion in Chemical Biology, 2007, 11:394-398.

Krawetz, et al., Large-Scale Expansion of Pluripotent Human Embryonic Stem Cells in Stirred-Suspension Bioreactors, Tissue Engineering: Part C, 2010, 16(4):573-582.

Liu, et al., Suspended Aggregates as an Immobilization Mode for High-Density Perfusion Culture of HEK 293 Cells in a Stirred Tank Bioreactor, Appl. Microbiol. Biotechnol., 2006, 72:1144-1151.

Nienow, et al., A Potentially Scalable Method for the Harvesting of hMSCs from Microcarriers, Biochemical Engineering Journal, 2014, 85:79-88.

Nienow, et al., Agitation Conditions for the Culture and Detachment of hMSCs from Microcarriers in Multiple Bioreactor Platforms, Biochemical Engineering Journal, 2016, 108:24-29.

Olmer, et al., Suspension Culture of Human Pluripotent Stem Cells in Controlled, Stirred Bioreactors, Tissue Engineering: Part C, 2012, 18(10):772-784.

Papantoniou, et al., The Release of Single Cells from Embryoid Bodies in a Capillary Flow Device, Chemical Engineering Science, 2011, 66:570-581.

Sart, et al., Three-Dimensional Aggregates of Mesenchymal Stem Cells: Cellular Mechanisms, Biological Properties and Applications, Tissue Engineering: Part B, 2014, 20(5):365-380.

Shafa, et al., Expansion and Long-Term Maintenance of Induced Pluripotent Stem Cells in Stirred Suspension Bioreactors, Journal of Tissue Engineering and Regenerative Medicine, 2012, 6:462-472.

Wang, et al., Scalable Expansion of Human Induced Pluripotent Stem Cells in the Defined Xeno-free E8 Medium Under Adherent and Suspension Culture Conditions, Stem Cell Research, 2013, 11:1103-1116.

Zur Nieden, et al., Embryonic Stem Cells Remain Highly Pluripotent Following Long Term Expansion as Aggregates in Suspension Bioreactors, Journal of Biotechnology, 2007, 129:421-432.

PCT International Search Report and Written Opinion, PCT/CA2017/050073, dated Apr. 11, 2017, 10 pages.

European Patent Office, Extended European Search Report, Application No. 17743516.1, dated Jun. 18, 2019, 6 pages.

\* cited by examiner

METHOD FOR DISSOCIATING CELL AGGREGATES

CROSS-REFERENCE TO RELATED APPLICATIONS

This application represents the national stage entry of PCT International Application No. PCT/CA2017/050073 filed Jan. 25 2017, which claims priority under the Paris Convention to U.S. Provisional Patent Application Ser. No. 62/287,103, filed Jan. 26 2016, both of which are incorporated herein by references if set forth in their entirety for all purposes.

FIELD OF THE DESCRIPTION

The present description relates generally to culturing cell aggregates in suspension. More specifically, the present description relates to dissociating cell aggregates within agitated reactors.

BACKGROUND OF THE DESCRIPTION

Suspension culture of cell aggregates is a well-known technique for expanding cell populations, such as, for example, pluripotent stem cells, multipotent stem cells, and various further and/or terminally differentiated cell types. Successful cell expansion in suspension culture has been demonstrated, for example, in murine[1,2,3] and human[4,5] embryonic stem cells (ESCs), as well as in murine[6,7] and human[8-10] induced pluripotent stem cells (iPSCs). Additional cell types that are amenable to aggregate suspension culture include, for example, neural stem and/or progenitor cells[11,12], mesenchymal stem cells[18] and differentiated cells, such as cardiomyocytes[13].

Traditionally, cell aggregate dissociation has been achieved by manually disrupting cell aggregates using a dissociation solution and pipetting. Pipette dissociation of cell aggregates is time consuming, poorly defined, and poorly controlled. The results of manual dissociation of cell aggregates are dependent on the skill of the operator and can be highly variable, at least in terms of cell recovery and cell viability.

In general, suspension culture of cell aggregates has been carried out at a scale suitable for research and development use. Larger scale cell culture is needed, for example, for process development, commercial production of cells, cell expansion for clinical trials and/or cell banking. As commercial production of cells in suspension increases, so will the need to dissociate cell aggregates at a larger scale. Manual cell aggregate dissociation has been applied to cells harvested from bioreactors[7,10,13,14]. However, manual cell aggregate dissociation is only effective when applied to a low number of cells (e.g., less than about $2\times10^8$ cells) provided in a low volume of liquid (e.g., less than about 25 mL).

It is desirable to obviate or mitigate one or more of the above deficiencies.

SUMMARY OF THE DESCRIPTION

In an aspect, a method for dissociating cell aggregates in an agitated reactor is provided. The method comprises: providing a cell culture comprising cell aggregates in the agitated reactor; contacting the cell aggregates with a dissociation reagent; generating a dissociation force in the agitated reactor; and exposing the contacted cell aggregates to the generated dissociation force under conditions sufficient to dissociate the contacted cell aggregates, thereby dissociating the exposed contacted cell aggregates in the agitated reactor.

In some embodiments, the contacting occurs before or at substantially the same time as the generating of the dissociation force in the agitated reactor. In some embodiments, the contacting occurs after the generating of the dissociation force in the agitated reactor.

In some embodiments, the dissociation force is generated by movement of a stirrer, impeller, paddle, or wheel, by rocking, or by forced fluid flow entering the agitated reactor.

In some embodiments, the providing step comprises exposing the cell culture to a culture force in the agitated reactor and wherein the dissociation force is about 50% to 500% of the culture force. In some embodiments, the dissociation force and the culture force are about equal.

In some embodiments, the method further comprising washing the cell culture prior to contacting the cell aggregates with the dissociation reagent. In some embodiments, the method further comprising neutralizing and/or diluting the dissociation reagent. In some embodiments, the method further comprising washing the dissociated cells.

In some embodiments, the method is carried out in a closed system.

In some embodiments, the agitated reactor is a stirred tank reactor, wave-mixed/rocking reactor, up and down agitation reactor, spinner flask, shake flask, shaken bioreactor, paddle mixer, or vertical wheel bioreactor, preferably a stirred tank reactor.

In some embodiments, the cell culture comprises a volume of about 50 mL-2,000 L, preferably between about 1 L to 1,000 L. In some embodiments, the cell culture comprises about $1\times10^6$ cells/mL to $1\times10^{15}$ cells/mL.

In some embodiments, the dissociated aggregates have a cell viability between about 50% and 100%, preferably greater than 90%. In some embodiments, the dissociated aggregates comprise aggregates that are at least 50% smaller than the provided cell aggregates. In some embodiments, the dissociated aggregates comprise substantially single cells. In some embodiments, the provided cell aggregates have a diameter of about 150 microns to 800 microns, preferably about 200 microns to 400 microns.

In some embodiments, the cell aggregates substantially comprise pluripotent stem cells. In some embodiments, the cell aggregates substantially comprise multipotent stem and/or progenitor cells. In some embodiments, the cell aggregates substantially comprise somatic cells.

In some embodiments, the dissociation force generated comprises a Kolmogorov eddy size less than the size of the largest cell aggregate and greater than the diameter of a cell in the cell aggregates at Reynolds number>1000. In some embodiments, the conditions comprise a time between about 2 minutes to 24 hours, preferably between about 10 minutes to 4 hours.

In an aspect, a method for passaging cells is provided. The method comprises: providing a cell culture comprising cell aggregates in a first agitated reactor; contacting the cell aggregates with a dissociation reagent; generating a dissociation force in the agitated reactor; exposing the contacted cell aggregates to the generated dissociation force under conditions sufficient to dissociate the contacted cell aggregates, thereby dissociating the exposed contacted cell aggregates in the first agitated reactor; and culturing at least a portion of the dissociated cell aggregates, thereby passaging the cells.

In some embodiments, the portion of the dissociated aggregates is cultured in the first agitated reactor. In some embodiments, the portion of the dissociated aggregates is cultures in a second agitated reactor. In some embodiments, the second agitated reactor is a different type of agitated reactor and/or is a different size than the first agitated reactor, preferably the second agitated reactor is larger than the first agitated reactor.

In an aspect, a method for generating dissociated differentiated cells from a stem or progenitor cell population within an agitated reactor is provided. The method comprises: providing a cell culture comprising a population of stem and/or progenitor cells in the agitated reactor; differentiating the stem and/or progenitor cells into differentiated cell aggregates within the agitated reactor under conditions suitable for differentiation; contacting the differentiated cell aggregates with a dissociation reagent; generating a dissociation force in the agitated reactor; and exposing the contacted differentiated cell aggregates to the generated dissociation force under conditions sufficient to dissociate the contacted differentiated cell aggregates, thereby generating the dissociated differentiated cells within the agitated reactor.

BRIEF DESCRIPTION OF THE DRAWINGS

The features of the invention will become more apparent in the following detailed description in which reference is made to the appended drawings wherein.

DETAILED DESCRIPTION OF THE NON-LIMITING EXEMPLARY EMBODIMENTS

Figures 1, 2:
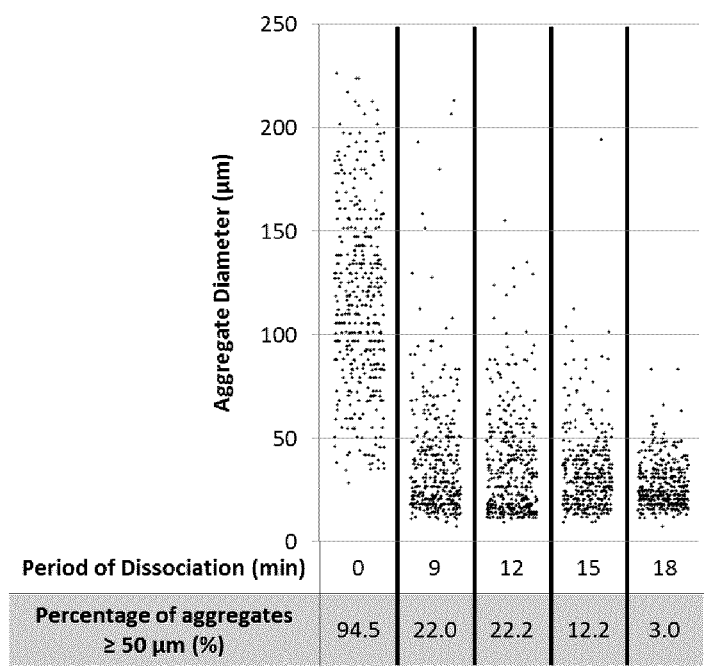
FIG. 1 depicts various features and embodiments of the method of cell aggregate dissociation provided herein (scale bars: 500 μm).
FIG. 2 depicts cell aggregate dissociation over time according to one embodiment of the method provided herein.

Unless defined otherwise, all technical and scientific terms used herein generally have the same meaning as commonly understood by one of ordinary skill in the art to which this invention belongs.

I. DEFINITIONS

As used herein, the terms "aggregate" and "cell aggregate" refer to a plurality of cells in which an association between the cells is caused by cell-cell interaction (e.g., by biologic attachments to one another). Biological attachment may be, for example, through surface proteins, such as integrins, immunoglobulins, cadherins, selectins, or other cell adhesion molecules. For example, cells may spontaneously associate in suspension and form cell-cell attachments (e.g., self-assembly), thereby forming aggregates, or cells may be forced to aggregate, for example by using AggreWell (Stem Cell Technologies) technology, centrifugation in multiwall plates (spin EB's), hanging drops, or other methods. In some embodiments, a cell aggregate may be substantially homogeneous (i.e., mostly containing cells of the same type). In some embodiments, a cell aggregate may be heterogeneous, (i.e., containing cells of more than one type), such as, for example, an embryoid body.

As used herein, the terms "passage" and "passaging" refer to the process of sub-culturing adherent cells, in which cell adhesion is disrupted and the cell density (number of cells per unit volume or area) is reduced by addition of fresh medium. Passaging is a technique that may be used to expand the number of cells in a culture and/or prolong the life of a cell line or the cells in culture.

As used herein, the term "expansion" refers to the proliferation of a cell, with or without differentiation, and may include no passaging, one passage or more than one passage and/or serial passages.

As used herein, the terms "dissociate" and "dissociation" refer to a process of separating aggregated cells from one another. For example, during dissociation, the cell-cell interaction between cells and between cells and extracellular matrix in the aggregate may be disrupted, thereby breaking apart the cells in the aggregate.

As used herein, the terms "dissociated" and "dissociated aggregate" refer to single cells, or cell aggregates or clusters that are smaller than the original cell aggregates (i.e., smaller than a pre-dissociation aggregate). For example, a dissociated aggregate may comprise about 50% or less surface area, volume, or diameter relative to a pre-dissociation cell aggregate.

As used herein, the terms "agitated reactor" and "agitated bioreactor" refer to a closed culture vessel configured to provide a dynamic fluid environment for cell cultivation. Examples of agitated reactors include, but are not limited to, stirred tank bioreactors, wave-mixed/rocking bioreactors, up and down agitation bioreactors (i.e., agitation reactor comprising piston action), spinner flasks, shaker flasks, shaken bioreactors, paddle mixers, vertical wheel bioreactors. An agitated reactor may be configured to house a cell culture volume of between about 2 mL-20,000 L.

As used herein, the term "dissociation reagent" refers to a solution comprising one or more agents that separate cells from one another, such as, for example, enzyme(s) and/or chelating agent(s). For example, a dissociation reagent may break the bonds between cells and/or between extracellular matrix proteins and cells, thereby disrupting the aggregation of cells in suspension. For example, a dissociation reagent may cause sequestration of a molecule to weaken or break bond formation between cell adhesion proteins (e.g. chelation to disrupt calcium dependent adhesion molecules), it may cause cleavage of proteins (e.g., serine proteases such as trypsin, collagenases, dispase, or papain) and/or other extracellular matrix components (e.g., hyaluronidase) to which cell surface molecules bind or within which cells becomes entrapped, and/or cleave such binding molecules from the cell surface (e.g., cleavage of integrins by serine proteases).

As used herein, the term "dissociation force" refers to the physical force required to dissociate an aggregate of cells. In operation, said dissociation force is applied to cell aggregates as a consequence of convective flow of the fluid in which the cells are suspended (e.g., the cell culture media). This flow may be effected by means of agitation applied to a bioreactor vessel system (e.g., agitation applied by movement of one or more stirrers, impellers, paddles, rocking, or wheels) housing the cell aggregates or by forced fluid flow entering the suspension system (e.g., by pumping). The magnitude (i.e., the size, extent, or dimensions) of the force required to dissociate cell aggregates using the method provide herein may depend on the degree of dissociation desired and/or the composition of the cell aggregates (e.g., cell type). In some embodiments, the dissociation force and the length scale (i.e., distance of effect) over which they act may be predicted utilizing equations describing mass/energy transport phenomenon and fluid dynamics (e.g., Kolmogorov length scale and Reynolds number, fluid dynamic modelling). In some embodiments, the magnitude and/or nature (e.g., intermittent or continuous) of the force to be applied for a particular population of aggregates may be determined empirically.

II. METHOD FOR DISSOCIATING CELL AGGREGATES WITHIN AN AGITATED REACTOR

The present description generally relates to a method for dissociating cell aggregates within an agitated reactor. Surprisingly, the inventors have discovered that cell aggregate dissociation can be achieved within an agitated reactor by contacting cell aggregates with a dissociating reagent and generating and applying a dissociation force to the cell aggregates in the agitated reactor, for example, by movement of a stirrer, impeller, paddle, rocking, or wheel, or by forced fluid flow. The inventors are not aware of any prior methods or systems described for dissociating cell aggregates, which involve combining a dissociation reagent with a dissociation force generated by a typical agitated reactor in order to dissociated cell aggregates within a reactor.

Previously, cell aggregate dissociation was typically achieved through manual manipulation (e.g., pipetting) in a dissociation solution. In this method, the combination of a dissociated reagent (typically an enzyme) and the fluid and shear forces effected by repeated passage of the suspension through the aperture of a pipette tip breaks apart cell aggregates. This technique can be highly variable, at least in terms of cell recovery and cell viability, and is only effective when applied to a low number of cells (e.g., less than about $2 \times 10^8$ cells) provided in a low volume of liquid (e.g., less than about 25 mL). Despite the drawbacks to manual cell aggregate dissociation, this technique has repeatedly been applied to cells harvested from bioreactors[7,10,13,14], wherein cells were dissociated manually in a solution volume of 1 mL[13] and 30 mL[14].

Some alternative methods for dissociating cell aggregates have been investigated and developed. For example, a capillary flow device was reported to induce dissociation of cell aggregates by applying a shear stress via the diameter of the capillary to the cell aggregate, which was reportedly sufficient to disrupt the cell aggregates in the absence of a dissociation reagent[15]. The authors of the capillary flow device paper stressed that a dissociation reagent should not be used in their method. The capillary flow device did result in cell aggregate dissociation, but less than sixty percent of the dissociated cells were viable[15]. Others have recognized a need to develop systems and methods for enabling cell aggregate dissociation within closed bioreactor systems. For example, WO 2016/113369 reported to address this problem by passing cell aggregates though a slicer grid, thereby chopping the cell aggregates into smaller-sized aggregates[16]. A reported method for closed-system passaging of pluripotent stem cell aggregates in a rocking platform bag bioreactor involves treating cell aggregates with an enzymatic dissociation agent and then pulling the treated cell aggregates into a syringe connected to a sampling port and dip tube[17]. The "pulling" of the cell aggregates through the aperture of the syringe provides a shear force sufficient to break the aggregates apart.

In contrast to the suggestion in the capillary flow paper[15] that a dissociating reagent should be avoided, the dissociation method provided herein involves use of a dissociating reagent. Dissociation of aggregates with a dissociation reagent is challenging, at least because in contrast to dissociation of cells from a surface, wherein only a monolayer of cells must be broken apart and from the surface, dissociation of cell aggregates requires disrupting the cell-cell associations between cells on the surface of the aggregate, and also between cells in the core of the aggregate. Further agitation of the cell culture may improve mass transfer of nutrients and oxygen within the culture, relative to static suspension culture. However, it is well-known that agitation may also cause fluid dynamics within the culture that may stress and/or damage cells grown in suspension.

The present results are surprising, at least because it was unexpected that contacting the cell aggregates with a dissociation regent while exposing the contacted aggregates to a dissociation force within an agitated reaction, was not only sufficient to dissociate the cell aggregates, but in some embodiments, it did not have a substantial negative impact on cell viability and/or yield. In some embodiments, the method herein may be used to achieve cell aggregate dissociation with cell viability levels of greater than 50%, greater than 55%, greater than 60%, greater than 65%, greater than 70%, greater than 80%, greater than 85%, greater than 90%, greater than 95% or greater than 96%. Further, in some embodiments, an additional device, such as a capillary flow device or a slicing grid, that is not typically provided in or with an agitated reactor, is not required to dissociate cell aggregates.

The present description generally relates to a method for dissociating cell aggregates within an agitated reactor having the following steps:
  providing a cell culture comprising cell aggregates in the agitated reactor;
  contacting the cell aggregates with a dissociation reagent;

generating a dissociation force in the agitated reactor; and exposing the contacted cell aggregates to the generated dissociation force under conditions sufficient to dissociate the contacted cell aggregates.

In some preferred embodiments, the disclosed method is suitable for use at large-scale (e.g., between about 1 L to 1,000 L) and/or in a closed agitated reactor system.

Each step in the disclosed method and various embodiments of the method are discussed in further detail below.

II(A): Providing a Cell Culture Comprising Cell Aggregates in the Agitated Reactor The method for dissociating cell aggregates comprises providing in an agitated reactor a cell culture comprising cell aggregates and a cell culture medium.

A skilled person will appreciate that it may be desirable to culture cell aggregates in a specific type of agitated reactor. For example, a user may elect to culture cell aggregates in a particular type of agitated reactor because they have a protocol that has been developed for use in a particular reactor type and/or size and/or having a particular impeller type. A user may elect to culture cell aggregates in a particular type of agitated reactor because they have access to a particular reactor type and/or size and/or having a particular impeller type, or because it fits in with pre-existing workflow. One advantage of the method provided herein is that in some of its embodiments, it is not limited to use in a specific type of agitated reactor (e.g., specific geometry, volume, impeller type etc.).

In some embodiments, the method for dissociating cell aggregates within an agitated reactor can be carried out in a stirred tank reactor (STR). In some embodiments, the method for dissociating cell aggregates within an agitated reactor can be carried out in a wave-mixed/rocking bioreactor. In some embodiments, the method for dissociating cell aggregates within an agitated reactor can be carried out in an up and down agitation reactor. In some embodiments, the method for dissociating cell aggregates within an agitated reactor can be carried out in a bioreactor spinner flask. In some embodiments, the method for dissociating cell aggregates within an agitated reactor can be carried out in a shake flask reactor. In some embodiments, the method for dissociating cell aggregates within an agitated reactor can be carried out in a shaken bioreactor. In some embodiments, the method for dissociating cell aggregates within an agitated reactor can be carried out in a paddle mixer reactor. In some embodiments, the method for dissociating cell aggregates within an agitated reactor can be carried out in a vertical wheel bioreactor.

In some embodiments, the volume of the culture vessel in the agitated reactor is from about 50 mL to about 20,000 L. In some embodiments, the volume of the culture vessel in the agitated reactor is from about 50 mL to about 2,000 L. In some embodiments, the volume of the culture vessel in the agitated reactor is from about 50 mL to about 200 L. In some embodiments, the volume of the culture vessel in the agitated reactor is from about 50 mL to about 100 L. In some embodiments, the volume of the culture vessel in the agitated reactor is from about 50 mL to about 50 L. In some embodiments, the volume of the culture vessel in the agitated reactor is from about 50 mL to about 20 L. In some embodiments, the volume of the culture vessel in the agitated reactor is from about 50 mL to about 10 L. In some embodiments, the volume of the culture vessel in the agitated reactor is from about 50 mL to about 1 L. In some embodiments, the volume of the culture vessel in the agitated reactor is from about 100 mL to about 10 L. In some embodiments, the volume of the culture vessel in the agitated reactor is from about 100 mL to about 5 L. In some embodiments, the volume of the culture vessel in the agitated reactor is from about 150 mL to about 1 L. In some embodiments, the volume of the culture vessel in the agitated reactor is from about 1 L to about 1,000 L.

A skilled person will appreciate that it may be desirable to culture cell aggregates comprising one or more different cell types. One advantage of the method provided herein is that in some of its embodiments, it is not limited to use with a specific cell type or cell aggregate type (e.g., pluripotent or somatic, homogenous or heterogeneous).

Culturing cells as aggregates in an agitated suspension culture is a known technique for expanding cell populations, such as, for example, murine or human ESCs, iPSCs, neural stem and/or progenitor cells, or differentiated cells, such as cardiomyocytes.

Various types of cell cultures are suitable for use in one or more embodiments of the disclosed method. For example, a cell culture comprising pluripotent stem cells (PSCs) in aggregate form, such as, for example, embryonic stem cells (ESCs), induced pluripotent stem cells (iPSCs), or adult stem cells, including human PSCs (hPSCs) may be suitable for use in the disclosed method. Non-pluripotent cells in aggregate form, such as, for example, adult somatic cells or terminally differentiated cells, including healthy cells and/or cells exhibiting one or more pathologies, may be suitable for use with the method provided herein. In one preferred embodiment, the cell culture suitable for use in the method provided herein comprises hPSC aggregates. In one preferred embodiment, the cell culture suitable for use in the method provided herein comprises human cardiomyocyte cell aggregates.

It is contemplated that one or more of the following cell types may be suitable for use in the method provided herein, such as, but not limited to: pluripotent stem cells and/or progeny thereof (such as, ecto- endo- and mesodermal progenitors; mesenchymal stem cells, cardiac cells (e.g., cardiomyocytes); musculo-skeletal cells (e.g., chondrocytes, osetocytes, osteoblasts, mycotes, tendynocytes); neural cells (e.g., neurons, astrocytes, retinal pigment epithelium cells (RPE cells), photoreceptors, macroglia); hepatic cells (e.g., hepatocytes, cholangiocytes); pancreatic cell (e.g., beta-cells, alpha-cells); adipocytes (e.g., white, brown, and beige fat); kidney cells (e.g., podocytes, duct cells); hormone secreting cells (e.g., thyroid gland cells, adrenal gland cells, pituitary cells); lung cells (e.g., clara cells, lung epithelial cells, alveolar cells); skin cells (e.g., keratinocytes, epidermal cells, basal cells, hair cells), or any of the aforementioned cells when not derived from pluripotent cells; mesenchymal stem and/or progenitor cells; neural stem and/or progenitors cells; fibroblasts; epithelial cells (e.g., skin epithelia, gut epithelia); endothelial cells (e.g., HUVEC, microvascular EC); and stromal cells.

Cell culture media suitable for maintaining the above cell types are known in the art and may be suitable for use in the method provided herein.

A skilled person will appreciate that it may be desirable to culture cell aggregates of a particular size (e.g., having a particular average diameter). For example, a user may elect to culture cell aggregates of a particular size because they have a protocol that calls for use of cell aggregates having a particular size. One advantage of the method provided herein is that in some of its embodiments, it is not limited to use of a cell aggregates having a specific size (e.g., a population having a specific average aggregate diameter, or range of diameters).

In some embodiments, cell cultures comprising aggregates having an average diameter of between about 150 and 800 micron in size prior to dissociation are suitable for use in the disclosed method. In some embodiments, cell cultures comprising aggregates having an average diameter no more than about 800 micron in size prior to dissociation are suitable for use in the disclosed method. In some embodiments, cell cultures comprising aggregates having an average diameter no more than about 600 micron in size prior to dissociation are suitable for use in the disclosed method. In some embodiments, cell cultures comprising aggregates having an average diameter no more than about 500 micron in size prior to dissociation are suitable for use in the disclosed method. In some embodiments, cell cultures comprising aggregates having an average diameter no more than about 400 micron in size prior to dissociation are suitable for use in the disclosed method. In some embodiments, cell cultures comprising aggregates having an average diameter no more than about 300 micron in size prior to dissociation are suitable for use in the disclosed method. In some embodiments, cell cultures comprising aggregates having an average diameter no more than about 200 micron in size prior to dissociation are suitable for use in the disclosed method. In some embodiments, cell cultures comprising aggregates having an average diameter no more than about 150 micron in size prior to dissociation are suitable for use in the disclosed method. In a preferred embodiment, cell cultures comprising aggregates having an average diameter of between about 300 and 500 micron in size prior to dissociation are suitable for use in the disclosed method. In a preferred embodiment, cell cultures comprising aggregates having an average diameter of between about 150 and 300 micron in size prior to dissociation are suitable for use in the disclosed method.

A skilled person will appreciate that it may be desirable to culture cell aggregates at a certain cell density. For example, a user may elect to culture cell aggregates at a certain density because they have a protocol that calls for use of cell aggregates having a particular density. One advantage of the method provided herein is that in some of its embodiments, it is not limited to use of a cell cultures having a specific density.

In some embodiments, the method for dissociating cell aggregates within an agitated reactor can be carried out with a cell density of at least about $5 \times 10^5$ cells/mL. For example, in some embodiments, the method for dissociating cell aggregates within an agitated reactor can be carried out with a cell culture volume of at least 2,000 L comprising at least $1 \times 10^{12}$ cells.

II(B): Contacting the Cell Aggregates with a Dissociation Reagent

The method further comprises contacting the cell aggregates in the agitated reactor with a dissociation reagent, such as, for example, a solution including one or more enzymes, such as Trypsin, EDTA, HyClone HyQTase, TrypLE™ Select, Accutase™, Accumax™, ReLeSR™, collagenase II, collagenase IV, or DNAse I or an enzyme-free dissociation reagent, such as Gentle Cell Dissociation Reagent™ or ZymeFree™.

A skilled person will appreciate that it may be desirable to contact cell aggregates with a particular type of dissociation reagent. For example, a user may elect to use a particular dissociation reagent because they have previous experience using a particular dissociation reagent and/or because a particular dissociation reagent is cost-effective. One advantage of the method provided herein is that in some of its embodiments, it is not limited to use of a specific dissociation reagent.

In some embodiments, the specific dissociation reagent used in the method may depend on the cell type to be dissociated and/or on the desired end product (e.g., single cells, smaller aggregates having a specific target diameter, etc.). The dissociation reagent may be provided in a diluent, such as, for example, phosphate buffered saline (PBS), Hank's balanced salt solution or ultrapure distilled water. The dissociation reagent may be provided at a concentration sufficient to degrade extracellular matrix (ECM) and/or weaken or break bonds between cell adhesion molecules and their binding partners, such as, for example, one or more of the concentrations set forth in Table 1. Specific concentrations of the dissociation reagent for use in the method provided herein may be determined by a skilled person.

TABLE 1

Examples of dissociation reagents that may be used alone or in combination to dissociate hPSCs and hPSC-derived cardiomyocytes in stirred tank reactors.

| Reagent | Concentration | Diluent |
| --- | --- | --- |
| TrypLE ™ Select | 1x, 0.5x | Phosphate buffered saline without calcium or magnesium |
| Accutase ™ | 0.5x | Phosphate buffered saline without calcium or magnesium |
| Accumax ™ | 0.5x | Phosphate buffered saline without calcium or magnesium |
| ReLeSR ™ | 0.5x | Phosphate buffered saline without calcium or magnesium |
| Collagenase II | 250 U/mL, 1000 U/mL, 1500 U/mL | Hank's balanced salt solution |
| Collagenase IV | 1000 U/mL | Hank's balanced salt solution |
| DNase I | 10 µg/mL, 20 µg/mL | UltraPure distilled water |

One advantage of using a dissociation reagent as part of a method for cell aggregate dissociation is that it may be easily incorporated into one or more pre-existing work flows that require cell aggregate dissociation. For example, a dissociation reagent may be added to a stirred tank reactor while agitation is stopped or while agitation is being carried out. Accordingly, in one embodiment, the method provided herein may be used in a closed system for cell culture. In one embodiment, the method provided herein may be used in an open system for cell culture. In some embodiments, addition of the dissociation reagent to the cell culture may be manual. In some embodiments, addition of the dissociation reagent to the cell culture may be automated or semi-automated.

In some embodiments, the dissociation reagent may be pre-determined. In some embodiments, the concentration of the dissociation reagent may be pre-determined.

In some embodiments, the method may further comprise a step of determining the dissociation reagent suitable for use in the method. For example, this determining step may comprise modelling, empirical testing, or a combination thereof.

In some embodiments, the method may further comprise a step of determining the concentration of the dissociation reagent suitable for use in the method. For example, this determining step may comprise modelling, empirical testing, or a combination thereof.

II(C): Generating a Dissociation Force in the Agitated Reactor

The method provided herein comprises generating a dissociation force in the agitated reactor that, in combination with exposure to the dissociation reagent, is sufficient to dissociate the cell aggregates.

In some embodiments, once the cell culture in the reactor has been contacted with a dissociation reagent, a dissociation force is generated in the agitated reactor. In some embodiments, the step of generating the dissociation force may precede the step of contacting the cell aggregates with a dissociation agent. In some embodiments, the step of generating the dissociation force and the step of contacting the cell aggregates with a dissociation agent may be carried out substantially simultaneously.

The dissociation force is generated by specifying an agitation rate (e.g., impeller speed or rocking rate) that corresponds to a particular fluid flow regime and intensity (e.g., turbulence, energy dissipation, length scale, or shear force) in the reactor. The specific dissociation force chosen may be dependent on the reactor system (e.g. type of mixing system, vessel dimensions, culture volume, etc.), the desired end product, cell type, and/or dissociation reagent.

A skilled person will appreciate that it may be desirable to generate a dissociation force having a particular agitation rate. For example, a user may elect to use a particular agitation rate because it is suitable for use in a particular reactor type and/or volume. For example, a user may elect to use a particular agitation rate because it is suitable for use with a particular cell type. One advantage of the method provided herein is that in some of its embodiments, it is not limited to use of a specific agitation rate.

In some embodiments, applying a dissociation force comprises adjusting the rate of agitation in the agitated reactor, from a first rate (which corresponds with the rate the cell aggregates are cultured at, referred to herein as a culturing force) to a second rate (which corresponds to a dissociation force). In some embodiments, the dissociation force may be greater than the force used to culture the cell aggregates in suspension.

Surprisingly, in some embodiments, the dissociation force may be about equal to the culture force. In some embodiments, the dissociation force may be less than the culture force.

In some embodiments, the dissociation force may be pre-determined. In some embodiments, the rate of the dissociation force may be pre-determined.

In some embodiments, the method may further comprise a step of determining the dissociation force suitable for use in the method. For example, this determining step may comprise modelling, empirical testing, or a combination thereof.

In some embodiments, the method may further comprise a step of determining the rate of the dissociation force suitable for use in the method. For example, this determining step may comprise modelling, empirical testing, or a combination thereof.

In some embodiments, a suitable dissociation force may be determined by a user by considering hydrodynamic parameters in the agitated reactor. For example, Kolmogorov eddy size and Reynold number are two hydrodynamic parameters that may be considered alone or in combination. In some preferred embodiments, the Kolmogorov eddy size is less than the largest cell aggregate, but greater than the diameter of a cell in the cell aggregates, such that the cell aggregates to be dissociated may be caught by the eddy and subjected to the force/energy dissipation of the eddy. In some preferred embodiments, the Reynold number is greater than 1000.

II(D): Exposing the Contacted Cell Aggregates to the Generated Dissociation Force Under Conditions Sufficient to Dissociate the Contacted Cell Aggregates.

The cell culture contacted with the dissociation reagent is exposed to the dissociation force in the reactor under conditions sufficient to dissociate the cell aggregates into smaller aggregates, cell clusters, and/or single cells, whichever is desired by the operator.

A skilled person will appreciate that it may be desirable to carry out aggregate dissociation under particular conditions. For example, a user may elect to dissociate the aggregates in a relatively short period of time because it is optimal for a particular workflow. For example, a user may elect to dissociate the cell aggregates at a particular temperature because it is the temperature used during one or more other steps in a work flow. One advantage of the method provided herein is that in some of its embodiments, it is not limited to dissociation under one or more specific conditions.

In this context, one example of a "condition" is time. Time may be dependent on the desired end product, dissociation reagent, cell type, hydrodynamic environment, and/or temperature. In some embodiments, the step of exposing the contacted cell aggregates to the generated dissociation force is not limited to a specific time period of exposure. In some embodiments of the method provided herein, the conditions of the exposing step include a time to dissociate aggregates that may range from about 3 minutes to 24 hours. In some embodiments the time is about 10 minutes to 4 hours. In some embodiments the time is about 5 minutes to 3 hours. In some embodiments, the time is about 9 minutes to 1 hour. In some embodiments, the time is about 18-35 minutes.

In some embodiments, the time period of exposure may be pre-determined.

In some embodiments, the method may further comprise a step of determining the time period of exposure suitable for use in the method. For example, this determining step may comprise modelling, empirical testing, or a combination thereof.

Another example of a "condition" is temperature. The temperature condition sufficient to dissociate the contacted cell aggregates may be dependent on the dissociation reagent (and enzyme kinetics thereof), size of the aggregate to be dissociated, composition of the aggregate (including cell type), and/or the desired end product. In some embodiments, the step of exposing the contacted cell aggregates to the generated dissociation force is not limited to a specific temperature during exposure. Rather, the cell culture contacted with the dissociation reagent should be exposed to the dissociation force in the reactor at a temperature sufficient to dissociate the cell aggregates. In some embodiments of the method provided herein, the conditions of the exposing step include a temperature for dissociating aggregates that may range from about 18° C. to 38° C. In some embodiments, the temperature is about equal to the temperature at which the cells are cultured in an agitated reactor.

In some embodiments, the temperature may be pre-determined.

In some embodiments, the method may further comprise a step of determining the temperature suitable for use in the method. For example, this determining step may comprise modelling, empirical testing, or a combination thereof.

The method for dissociating cell aggregates in an agitated reactor provided herein may be further optimized for use with various cell types, cell culture protocols, agitated reactor types, etc.

As set forth herein, it will be understood and appreciated that parameters influencing the degree of aggregate dissociation and/or the extent to which aggregates are dissociated into smaller aggregates, small clusters and/or single cells (i.e., the percentage of the cell populations that reaches dissociation) may include, but are not limited to: (1) the dissociation reagent used and concentration of its constituent (s); (2) the intensity of agitation (e.g., power input, impeller tip speed, impeller speed, rock rate, rock angle, shear rate, Reynolds number, etc.); (3) geometry of the reactor vessel; (4) mixing mechanism (e.g., impeller type); (5) duration of the dissociation process; and/or (6) temperature. In some embodiments, one or more of these parameters may be pre-determined. In some embodiments, the method may further comprise one or more steps of determining one of these parameters suitable for use in the method. For example, these one or more determining steps may comprise modelling, empirical testing, or a combination thereof.

In operation, the choice of reactor geometry and mixing mechanism may be based on requirements for cultivating cells (e.g., cell type, desired cell number, cell differentiation or maturation protocol etc.).

In operation, fluid dynamic parameters, such as Kolmogorov eddy length, Reynolds number, and/or shear rates may be calculated on the basis of the geometry/mixing mechanism, fluid physical properties (e.g., viscosity and density), and agitation rate/intensity.

Due to the number of parameters to be investigated, and potential for a plurality of parameter levels (e.g., a plurality of dissociation reagents and concentration combinations are possible), using the disclosed novel and inventive method, which comprises:

providing a cell culture comprising cell aggregates in the agitated reactor;
contacting the cell aggregates with a dissociation reagent;
generating a dissociation force in the agitated reactor; and
exposing the contacted cell aggregates to the generated dissociation force under conditions sufficient to dissociate the contacted cell aggregates,
a skilled person may optimize the cell aggregate dissociation method provided herein for use with a specific cell type. For example, one skilled in the art might first conduct a pilot experiment using an intermediate value (e.g., a dissociation force that is about equal to the force used to culture the cell aggregates in the agitated reactor) for agitation rate to screen a plurality of dissociation reagents, with sampling (e.g., to determine aggregate size and/or cell viability) at regular intervals over the full duration of the experiment (e.g., every 10 minutes for a total for 30 minutes). Such a pilot experiment might be conducted at a nominal temperature of 37° C., as this is the typical cultivation temperature for most human cell types.

In another example of optimization, reactor geometry and mixing mechanism may be determined based on culture requirements for a desired cell type, and five different dissociation reagents are of interest, an optimization experiment conducted in triplicate would require 15 runs to test the conditions of interest. Based on percent dissociation and cell viability relative to duration of the process, the skilled person could then identify either a single preferred dissociation reagent, or 2-3 top candidate dissociation reagents. In another example of optimization, the two top dissociation reagent candidates are selected, the impact of varying agitation rate and duration could be quantitatively examined using, for example, a full-factorial experimental design. Run in triplicate, with 3 levels each for agitation rate (low, medium, high) and duration (bracketing a mid-point based on pilot study results), 54 runs in total would be required. Data analysis would permit construction of mathematical models from which "optimum" process conditions may be estimated. The impact of variables, such as, but not limited to, wash vs. no wash and temperature may then be evaluated in subsequent experiments using this initial 'optimum' as a reference condition.

It will be appreciated by a person of skill in the art that other forms of experimental design, or overall approach, might also be used to optimize the method for dissociating cell aggregates provided herein. For example, it is common for a discrete step in a larger process to be subject to multiple constraints or requirements. For example, a user may require that cell aggregate dissociation be completed within a maximum of 10 minutes, but there may be some tolerance for loss in cell viability in the process. In that case, agitation intensity and/or dissociation reagent concentration may be increased to accelerate the dissociation process. In another example, reagent choice may be limited by cost considerations or presence of undesirable components (e.g., those of animal origin). In that case, a dissociation reagent that results in sub-optimal cell-viability post-dissociation may be chosen to reduce costs. By considering the context in which the disclosed method of cell aggregate dissociation will be operated, such as, but not limited to, constraints, requirements, tolerances, etc., a skilled person may establish an acceptable design to explore the impacts of changing parameters, thereby optimizing the method of cell dissociation provided herein.

In one embodiment, the method for dissociating cell aggregates within an agitated reactor can be carried out in an open system.

In one embodiment, the method for dissociating cell aggregates within an agitated reactor can be carried out in a closed system. This may be advantageous for one or more of the following reasons: a closed system may reduce risk of contamination, maintain the culture environment (e.g., DO, pH, temperature etc.), facilitate operations in less stringent environments (e.g., lower-grade clean rooms), reduce labour, facilitate automation, etc.

In some embodiments, prior to contacting the cell culture with a dissociation reagent, the cell culture is washed. Washing may remove one or more agents that may inhibit the dissociation reagent. For example, cell aggregates may be concentrated and then washed to remove spent media. Washed cells may then be re-suspended in a diluted solution comprising the dissociation reagent. Washing may be carried out in a closed or open system. In some embodiments, the cell culture may be removed from the agitated reactor for washing and the washed cells may be returned to the agitated reactor following washing. In one embodiment, the wash step may be carried out within the agitated reactor.

The methods provided herein enable several workflows, such as, for example, passaging, serial passaging, generation of mature cells from stem and/or progenitor cells, and/or use of the dissociated cell aggregates in cell process development, cell expansion for clinical trials, therapeutics and/or cell banding, as described further below.

III. METHOD FOR PASSAGING CELLS

A method for passaging cells is provided. Generally, the method comprises:
  providing a cell culture comprising cell aggregates in the agitated reactor;
  contacting the cell aggregates with a dissociation reagent;
  generating a dissociation force in the agitated reactor;
  exposing the contacted cell aggregates to the generated dissociation force under conditions sufficient to dissociate the contacted cell aggregates; and
  culturing the dissociated cell aggregates, thereby passaging the cells within the agitated reactor.

In some embodiments, one or more subsequent steps of contacting the "once-dissociated cell aggregates" (i.e., those passaged one time) with a dissociation reagent, generating a dissociation force to dissociate the cell aggregates and culturing the "twice-dissociated cell aggregates" (i.e., those passaged two times) in an agitated reactor may be carried out in order to facilitate serial passaging of cells. One or more, further steps may be taken in various embodiments of the method of cell passaging.

For example, in some embodiments, cell aggregates are cultured in an agitated reactor for a period of time. At the end of the culture period, cell aggregates may be washed to remove inhibiting agents and then contacted with a dissociation reagent within the agitated reactor. A dissociation force is then generated in the agitated reactor. The dissociation force should be sufficient to dissociate the cell aggregates into cell clusters and/or single cells, whichever is desired by the operator. The dissociation force may be pre-determined or determined by a user, for example, as set forth herein. The dissociation force is applied to the cell aggregates under conditions sufficient to dissociate the cell aggregates. The dissociation reagent in the cell culture may then be neutralised or diluted. In some embodiments, a cell count is performed to determine the number of cells available for passaging. A portion of, or the full culture, may then be washed to remove the dissociation reagent. A desired number of cells may be re-suspended in fresh culture medium to achieve a desired inoculation density (as determined by the user). Finally, the cells may be re-inoculated into a reactor for a subsequent culture period.

In some embodiments, the reactor used for a subsequent culture period may be the same reactor used to culture and dissociate the cell aggregates initially. In some embodiments, the reactor used for a subsequent culture period may be a different reactor than the reactor used to culture and dissociate the cell aggregates initially. In some embodiments, wherein the reactor used for subsequent culture is a different reactor, it may be the same type of agitated reactor or a different type of reactor than the reactor used to culture and dissociate the cell aggregates initially. In some embodiments, wherein the reactor used for subsequent culture is a different reactor, it may be the same size agitated reactor or a different size reactor than the reactor used to culture and dissociate the cell aggregates initially, the different size reaction being smaller in some embodiments and larger in other embodiments.

In one preferred embodiment, for large scale production, the reactor suitable for use in the second or subsequent culture period(s) is a larger reactor than the reactor used for initial culture and dissociation. In one preferred embodiment, multiple reactors are inoculated in parallel for use in the second or subsequent culture period(s), thereby facilitating parallel serial passaging.

In some embodiments, serial passaging of the cell aggregates is enabled by disassociation of the cell aggregates in a closed system using the method provided herein. In some embodiments, serial passaging of the cell aggregates is enabled by disassociation of the cell aggregates in an open system using the method provided herein.

IV. METHOD FOR GENERATING MATURE CELLS FROM STEM OR PROGENITOR CELL POPULATIONS WITHIN AN AGITATED REACTOR

A method for generating and/or harvesting mature cells from a stem and/or progenitor cell population within an agitated reactor is provided. Generally, the method comprises:
  providing a cell culture comprising a population of stem and/or progenitor cells in an agitated reactor;
  differentiating the stem and/or progenitor cells into mature cells within the agitated reactor, wherein the mature cells form aggregates;
  contacting the mature cell aggregates with a dissociation reagent;
  generating a dissociation force in the agitated reactor sufficient to dissociate the mature cell aggregates; and
  exposing the contacted mature cell aggregates to the generated dissociation force under conditions sufficient to dissociate the contacted mature cell aggregates.

In some embodiments, the dissociated mature cells are harvested.

For example, in one embodiment, stem and/or progenitor cells are differentiated into a mature progeny (e.g. hPSC are differentiated to cardiomyocytes) within an agitated reactor. Once the desired differentiated progeny are achieved in the culture, cultures may be harvested using the dissociation method described herein. Aggregates of mature cells may be washed to remove inhibiting agents, and then contacted with a dissociation reagent within the agitated reactor. A dissociation force is then generated in the agitated reactor. The dissociation force should be sufficient to dissociate the cell aggregates into cell clusters and/or single cells, whichever is desired by the operator. The dissociation force is applied to the aggregates within the appropriate conditions (e.g., 37° C.) for an appropriate time until the final product (cell clusters and/or single cells) is achieved. The dissociation reagent may then be neutralised or diluted. A cell count may be performed to determine the number of cells in the culture. The full culture may then be washed to remove the dissociation reagent and utilised for an end product (e.g., cryopreserved product, tissue engineering, drug screening, cell therapy, etc.).

Prior methods for harvesting mature cells are typically labour-intensive and multi-staged, and may require multiple batches if the cultures contained greater than $2.0 \times 10^8$ cells. Using the dissociation method described herein, in some embodiments, dissociation of mature cell aggregates and subsequent harvesting of dissociated mature cells could be performed in a single batch, requiring relatively less operator interference.

V. USE OF THE DISCLOSED METHOD

It is contemplated that the methods described herein may be used, for example, to generate cells for research applications, therapeutic and/or diagnostic testing, therapeutic treatment of patients, and/or for generating banks of cells.

In some embodiments, methods comprising administering to subjects in need thereof a pharmaceutical composition comprising a pharmaceutically-acceptable carrier and at least one cell obtained from the methods described herein are provided.

In some embodiments, a method of treating a disorder in a subject in need of treatment by administering a therapeutically effective amount of the cells produced in the methods above to the subject in need thereof is provided. In some embodiments, these methods may further include a method of treating a disorder in a subject in need of treatment by administering a therapeutically effective amount of a pharmaceutical composition comprising a pharmaceutically-acceptable carrier and the cells produced in the methods provided herein. It will be understood that the methods described herein may be applicable to pluripotent stem cells, multipotent stem and/or progenitor cells, and/or differentiated cells.

The invention will be more fully understood upon consideration of the following non-limiting Examples.

VI. EXAMPLES

Example 1

Development of a Method for Dissociating Human Pluripotent Stem Cell (hPSC) Aggregates in Stirred Tank Reactors Materials and Methods:
Cell Line The ES02 cell line (WiCell International) adapted to single cell passaging on mouse embryonic fibroblasts (MEFs) with TrypLE™ Select (referred to as "HES2") and the ESI-17 cell line (ESI BIO) were used.

Adherent hPSC Culture

HES2 cells were cultured on a layer of mitotically-inactivated MEFs in HES media supplemented with fibroblast growth factor 2 (FGF2). Briefly, HES2 cells were thawed and seeded into wells containing a layer of mitotically-inactivated MEFs. Cells were cultured at 37° C., 5% $CO_2$ in HES medium supplemented with FGF2. A full medium exchange was performed daily. When cultures were 80-90% confluent, cultures were harvested with TrypLE™ Select (Thermo Fisher Scientific). Cells were seeded as single cells onto mitotically-inactivated MEFs and cultured as previously described or inoculated into suspension cultures in mTeSR™1 (Stem Cell Technologies) supplemented with Y-27623 (TOCRIS Bioscience).

ESI-17 cells were cultured on a layer of Matrigel™ (VWR) in mTeSR™1. Briefly, ESI-17 cells were thawed and seeded into wells coated with Matrigel™ for 1 hour prior to use. Cells were cultured at 37° C., 5% $CO_2$ in mTeSR™1. A full medium exchange was performed daily. When cultures were 80-90% confluent, cultures were passaged. For adherent culture, cells were harvested with Gentle Cell Dissociation Reagent™ (Stem Cell Technologies) and seeded as small cell clusters onto Matrigel™-coated plates/flasks. For suspension cultures, cells were pre-treated with Y-27623 prior to harvest with TrypLE™ Select, and then inoculated into suspension cultures in mTeSR™1 supplemented with Y-27623.

Suspension Aggregate-Based hPSC Culture

Cells were cultured in either rectangular vessels without sparge tubes using the ambr™15 cell culture system (Sartorius Stedim), which was configured to house a 15 mL culture, or in the cylindrical MiniBio 500 bioreactor system (Applikon), which was configured to house a 150 mL culture. All bioreactors were equipped with marine impellers. Cells were inoculated in mTeSR™1 supplemented with Y-27632. A partial medium exchange was performed daily using fresh mTeSR™1. In the ambr™15 system, the medium exchange was performed manually. In the MiniBio 500 system, the medium was perfused continuously using the BioSep perfusion device (Applikon). Cultures were maintained for up to 7 days prior to harvest or passage. Dissolved oxygen was controlled by air, nitrogen or oxygen gas. Temperature was controlled to 37° C.

Dissociation in Stirred Tank Reactors (STRs)

ReLeSR™ (Stem Cell Technologies), Accutase™ (Innovative Cell Technologies), Accumax™ (Innovative Cell Technologies), or TrypLE™ Select, was diluted with an equivalent volume of phosphate buffered saline (PBS) without magnesium or calcium and supplemented with 10 μg/mL of DNase I (Calbiochem). Aggregates were manually concentrated, washed with PBS, and re-suspended in the diluted dissociation reagent. Aggregates were then dissociated by agitation at 450 rpm down-stir in an ambr™15 vessel or at 150 rpm in a MiniBio 500 for up to 30 minutes at 37° C. The progress of dissociation was monitored by visual inspection. Dissociation was considered complete when less than 5% of the culture contained cell clusters>50 μm. When dissociation was complete cultures were diluted with 3 times the volume of DMEM-F12 containing 10 μg/mL of DNase I.

For a closed dissociation process, the SonoSep (SonoSep Technologies) concentration and wash device was integrated into the MiniBio 500 dissociation process for the concentration and wash steps. Aggregates were concentrated in the SonoSep device using a flow rate of 5 mL/min, power of 4 W, and a run:settle cycle of 2 min:10 s. The aggregates collected in the cell reservoir were then washed using a flow rate of 2 mL/min, power of 2 W, and a run:settle cycle of 5 min:30 s. Aggregates were washed with 50 mL of PBS. Aggregates were then re-suspended in the diluted dissociation reagent and re-introduced into the MiniBio 500 at a flow rate of 2 mL/min. Dissociation in the closed process was performed as stated above.

Culture Assessment: Sampling from STR Systems

Samples were removed without disrupting the operation or control of the STR systems using the ambr™15 liquid handler or the sample port of the MiniBio 500 systems, respectively. Samples were dispensed into an ultra-low attachment 24-well or 6-well plate and imaged.

Culture Assessment: Aggregate Sizing

Samples were dispensed into an ultra-low attachment 24-well plate and imaged using an inverted light microscope at 4× magnification (EVOS™ XL Core Cell Imaging System). Using ImageJ (1.47v), aggregates/cells were manually fitted with ellipses. The mean diameter of each sample was determined using the arithmetic average of the major and minor axes of 250 cells and/or cell clusters in the sample.

Culture Assessment: Cell Enumeration and Viability

Cells were enumerated using the NucleoCounter™ NC-200™ automated cell counter. Using the Vial-Cassette™, all cells were stained with acridine orange and dead cells counterstained with DAPI, thus providing a measurement of total cell density and viability. The total number of viable cells in the STR was extrapolated from the sample taken to calculate the fold expansion (Equation 1).

Fold $Expansion_t = N_t/N_0$ (Equation 1) wherein $N_t$ and $N_0$ are the total number of viable cells in a reactor at the end and beginning of the culture process, respectively.

Culture Assessment: Flow Cytometry

For assessment of pluripotency, the expression of 4 pluripotent markers (Tra-1-60, SSEA4, Oct4, and Sox2) by hPSCs was measured. Briefly, cells were fixed with 2% paraformaldehyde and stored in FACS Wash Buffer at 4° C. until staining. All samples from time points of a single biological replicate were stained and analysed together within 2 weeks of fixation. Samples were permeabilised in 0.1% Triton X-100, then stained with α-Tra-1-60, α-SSEA4, α-Oct4, and α-Sox2 (BD Biosciences). Data acquisition was performed on an LSR Fortessa™ Flow Cytometer (BD Biosciences). Samples were analysed using FlowJo™ software (vX.0.7) and positive pluripotency expression was determined based on unstained (negative) controls.

Statistics

For data sets containing 3 or more biological replicates, data are presented as the mean±standard deviation.

Results:

To develop a method to dissociate hPSC aggregates into single cells (or cell clusters containing fewer than 5 cells) in STRs, the efficacy of four dissociation reagents to dissociate aggregates under agitation was evaluated. The reagents tested were 10 μg/mL of DNase I and 50% ReLeSR™, 50% TrypLE™ Select, 50% Accutase™, or 50% Accumax™ in PBS. Aggregates were re-suspended in one of the four reagents and agitated at 37° C. in an ambr™15 STR system. Cultures were agitated at 450 rpm to generate a hydrodynamic environment where the maximum shear stress was 0.37 Pa and the Kolmogorov eddy length was 101 μm. Dissociation progress was visually assessed every 5 minutes. After 25 minutes, the dissociation reagents were diluted and cultures were evaluated for viability and the percentage of cell clusters containing 5 or more cells. At this time the majority of the culture was dissociated (i.e., <10% cell clusters were present in the cell culture) irrespective of the reagent used (FIG. 1). Aggregates were slower to dissociate in ReLeSR™ compared to the other dissociation reagents tested, as evidenced by the large aggregates observed after 20 minutes of agitation (FIG. 1). Viability of the ReLeSR™ culture (81.7%) was lower than the TrypLE™ Select, Accumax™ and Accutase™ cultures (95.2%, 92.4% and 93.1%, respectively). TrypLE™ Select was the most cost-effective reagent. Thus, 10 μg/mL of DNase I and 50% TrypLE™ Select in PBS were used for further development of the cell aggregate dissociation method.

Next, experiments to verify whether or not the dissociation method adversely affected pluripotency of the dissociated hPSCs were carried out. Three batches of HES2 hPSC aggregates were dissociated in 10 μg/mL of DNase I and 50% TrypLE™ Select in PBS under agitation at 450 rpm for 21-22 minutes at 37° C. in the ambr™15 system. Dissociation progess was visually assessed after 9 minutes of dissociation and every 3 minutes thereafter. After dissociation was complete, cultures were assessed for viability, the percentage of the culture not in single cells (i.e. remaining in cell clusters containing 5 or more cells) and the percentage of cells expressing the pluripotent markers, Tra-1-60, SSEA4, Oct4, and Sox2. Cells were then re-inoculated and expanded in the ambr™15 system for 4 days before re-assessing the pluripotency of the culture. The time required for dissociation (21.8±0.2 minutes, n=3) and the viability post-dissociation (98.3±0.7%, n=3) were consistent (Table 2). The percentage of the culture not in single cells (i.e., percentage of cell clusters comprising 5 or more cells) varied from 1-8%. Pluripotency of the cells was not adversely affected by the dissociation method (Table 2). The pluripotency of cells in Batch 1 and 3 fluctuated 4-6% after 4 days of culture, which is within the range typically seen in standard adherent cultures from passage to passage (±10%).

In Batch 2, the starting quality of the culture (i.e., pluripotency) was low (37.0%) (Table 2). The dissociation process did not adversely affect the hPSCs or their differentiated progeny. However, as differentiated cells do not proliferate as quickly as the hPSCs, the ratio of hPSCs to differentiated progeny increased throughout the subsequent 4 day culture period. As such, at the end of the culture period, the percentage of pluripotent cells had increased to 75.6% (Table 2).

TABLE 2

Product outputs of 3 batches of HES2 hPSC aggregates post-dissociation.

| | | 0 h post-dissociation | | | 96 h post-dissociation |
|---|---|---|---|---|---|
| | Time to dissociate aggregates (min) | Viability (%) | Percentage of cell clusters (≥5 cells) (%) | Pluripotent population (% Tra-1-60$^+$SSEA4$^+$ Oct4$^+$Sox2$^+$) | Pluripotent population (% Tra-1-60$^+$SSEA4$^+$ Oct4$^+$Sox2$^+$) |
| Batch 1 | 22.0 | 99.0 | 8 | 90.7 | 96.3 |
| Batch 2 | 21.5 | 98.4 | 1 | 37.0 | 75.6 |
| Batch 3 | 22.0 | 97.4 | 2 | 73.0 | 69.4 |

Aggregate diameters were measured at discrete time points during the dissociation of Batch 3. Twenty-two percent of the cell culture remained larger than 50 μm (approximately 3-5 cells in width) after 9 minutes of agitation (FIG. 2). Full dissociation was achieved after 22 minutes (Table 2), at which time less than 2% of the culture comprised cell clusters containing 5 or more cells (i.e., cell clusters approximately 2-3 cells in width).

These results support a method for consistently and effectively dissociating hPSC aggregates in a STR. The method, using a TrypLE™-based solution, was shown to consistently dissociate aggregates to yield a final product with >90% viability and <10% of cells remained in clusters. The dissociation method did not adversely affect the pluripotency of the final product. This method was also effective independent of the quality (i.e., starting pluripotency) of the cell aggregates.

Example 2

Application of Dissociation Method for Passaging and Continuous Expansion in Stirred Tank Reactors The dissociation method of Example, was carried out in the MiniBio 500 STR system to passage hPSC aggregates for continuous expansion at a scale of 100-150 mL.

In the MiniBio 500 system, an agitation of 150 rpm was used to generate a hydrodynamic environment wherein the maximum shear stress was 0.13 Pa and the Kolmogorov eddy length was 169 μm. Two hPSC lines, HES2 and ESI-17, were expanded as aggregates over 5 passages in the MiniBio 500. Passaging was accomplished by agitating the aggregates in 10 μg/mL of DNase I and 50% TrypLE™ Select in PBS at 37° C. for 13-19 minutes in the MiniBio 500. After dissociation was complete, cells were enumerated and then re-inoculated into the MiniBio 500. The fold expansion and pluripotency (% Tra-1-60$^+$SSEA4$^+$Oct4$^+$Sox2$^+$) of the cells were assessed at the end of each passage, and cell karyotype was analysed at the end of passage 4.

Figure 3:
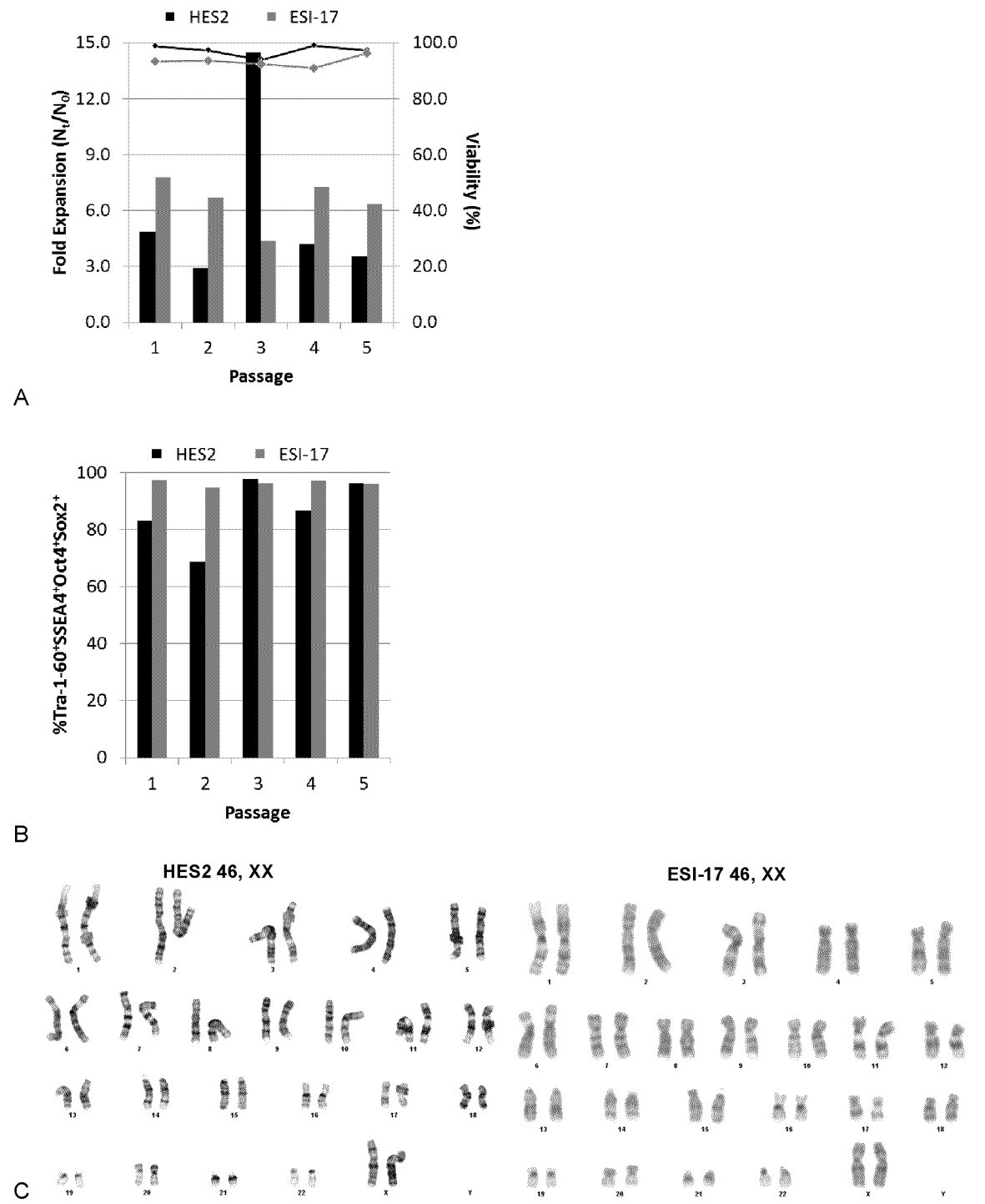
FIG. 3 depicts evaluation of two hPSC cell lines subjected to one embodiment of the method provided herein; HES2 (black) and ESI-17 (grey) hPSCs were expanded in a MiniBio 500 over 5 continuous passages without any adverse effects to the: (A) fold expansion, viability; (B) pluripotency; or (C) karyotype (left HES2 46, XX; right ESI-17 46, XX).

Dissociation of hPSC aggregates in the MiniBio 500 did not adversely affect the viability, proliferative capacity, pluripotency or the karyotype of either HES2 or ESI-17 hPSCs (FIG. 3). Cell viability post-dissociation was greater than 90% for both HES2 and ESI-17 hPSCs at all passages (FIG. 3). Variation in the fold expansion (FIG. 3A) and pluripotency (FIG. 3B) was observed in both the HES2 and ESI-17 cell lines during the first 3 passages. These variations were attributed to adaptation of the hPSCs from adherent culture to aggregate-based suspension culture rather than the dissociation.

Example 3

Application of Dissociation Method to a Closed System

The dissociation method of Example 1 was applied in a closed system by integrating the SonoSep concentration and wash device with the MiniBio 500.

The time required for dissociation, cell viability post-dissociation, and the percentage of remaining clusters of 5 or more cells were similar in the closed system (SonoSep integrated with MiniBio 500) and the open system (MiniBio 500 with manual concentration and wash) (Table 3). These results support application of the method for dissociating cell aggregates provided herein for passaging cells, thereby making possible continuous manufacture of hPSCs in a closed system, which may be automated.

TABLE 1

Post-dissociation product outputs of HES2 hPSC aggregates concentrated and washed manually or concentrated and washed with SonoSep device.

|  | Manual | SonoSep |
|---|---|---|
| Time to dissociate aggregates (min) | 19 | 19 |
| Viability (%) | 97.0 | 98.7 |
| Percentage of cell clusters (≥5 cells) (%) | 6 | 2 |

The method was successfully applied in the MiniBio 500, at a volume of 150 mL, to dissociate a relatively large number of cell aggregates (e.g., comprising up to $3.2 \times 10^8$ cells) in a single and automated process. This enabled continuous expansion of 2 hPSC lines over 5 passages without adverse effects on proliferative capacity, pluripotency, or karyotype. Further, it was demonstrated that the process could be closed by integrating a concentration and wash device with the MiniBio 500 system. Thus, dissociation of aggregates within an STR using the present method improves upon manual dissociation methods by enabling single batch dissociation of a large number of aggregates, thereby removing operator dependence and decreasing contamination risks by implementing a closed process.

Example 4

Application of Dissociation Method for Generation of Cardiomyocyte Cell Suspensions from hPSCs in STRs Materials and Methods Suspension Aggregate-Based Cardiomyocyte Differentiation Cells were differentiated in a cylindrical MiniBio 500 bioreactor system equipped with a marine impeller. Human PSCs were expanded prior to differentiation. To induce differentiation, hPSC aggregates were removed from culture, washed with DMEM-F12, and differentiated into cardiomyocytes in a three-stage process (Witty, A. D. et al. Generation of the epicardial lineage from human pluripotent stem cells. *Nat. Biotech.* 32, 1026-1035 (2014)). Aggregates were cultured in Stage 1 medium for 2 days, Stage 2 medium for 2 days, and then Stage 3 medium without VEGF for 9 days. During the third stage, the medium was fully replaced every 2 days. All medium exchange steps were performed manually. The dissolved oxygen was controlled by air, nitrogen or oxygen gas. The temperature was controlled to 37° C.

Manual Dissociation of hPSC-Derived Cardiomyocyte Aggregates

Aggregates were washed once with Hank's Buffered Salt Solution (Thermo Fisher Scientific) supplemented with 10 μg/mL of DNase I. Aggregates were then incubated in 1000 U/mL of Collagenase, Type II (Worthington) for 2 hours at 37° C. Aggregates were gently pipetted to dissociate the larger aggregates. Aggregates were then re-suspended and incubated in TrypLE™ Select supplemented with 10 μg/mL of DNase I for 10 minutes at 37° C. Aggregates were dissociated with a micropipette. Cells were then diluted 2-fold with FACS Wash Buffer.

Assessment of Cardiomyocytes

For assessment of cardiomyocytes, the expression of cardiomyocyte marker, cardiac troponin T (cTnT), was measured. Briefly, cells were fixed and permeabilised as described above. Cells were then stained with mouse IgG$_1$ α-cTnT (Thermo Fischer Scientific), followed by α-mouse IgG$_1$-Alexa fluor-488 (Thermo Fischer Scientific). Data acquisition was performed on the LSR Fortessa Flow Cytometer. Samples were analysed using FlowJo software and positive cTnT expression was determined based on a secondary only control.

Dissociation of hPSC-Derived Cardiomyocyte Aggregates in a MiniBio 500

The dissociation method of Example 1 was applied to generate, dissociate and harvest cardiomyocytes from the MiniBio 500 STR system. ESI-17 hPSC were expanded and differentiated into cardiomyocytes in the MiniBio 500. After 12 days of differentiation, cells were assessed for the expression of cardiomyocyte marker, cardiac troponin T (cTnT), to ensure that the differentiation was successful (>70% cTnT$^+$). Cardiomyocyte aggregates were then dissociated on the following day in 10 μg/mL of DNase I and 50% TrypLE™ Select in PBS under agitation at 150 rpm for 21 minutes at 37° C. in the MiniBio 500 system. After dissociation, cells were harvested, enumerated, and plated on gelatin. Cells were re-assessed 1 day after plating for total number of viable cells and expression of cTnT.

Dissociation of hPSC-Derived Cardiomyocyte Aggregates in an Ambr™15 Bioreactor:

ESI-17 PSCs were differentiated to cardiomyocytes for 15 days, resulting in a mean aggregate diameter of 140 μm. The cardiomyocyte aggregates were resuspended in 24 mL of warm 1 mg/mL Collagenase II (Worthington) in Hank's Balanced Salt Solution (HBSS, Thermo Fisher) at an approximate cell density of $1.6 \times 10^6$ cells/mL, and 8 mL of aggregate/collagenase suspension was added to each of three Ambr vessels. The vessels were loaded into the reactor, and the Ambr was set to the following settings: agitation rate=downstir 450 rpm, DO=90%, temperature=37° C.

For the first 2 hours, samples (200 μL) were removed every 30 minutes from each vessel using a liquid handler and transferred to a 24-well ultralow attachment plate (Corning) containing 400 μL DMEM/F12 supplemented with 10% FBS and 10 μg/mL DNAse I. Cell suspensions were triturated by pipetting gently 10 times with a P1000 to ensure appropriate sampling from a well-mixed suspension. Images of the dissociated cultures were captured using an inverted microscope and for samples that appeared close to dissociated, a sample was counted for % viability, viable cell density (VCD) and % aggregates using a NucleoCounter NC-200. Dissociation was considered to be complete when the average % aggregates remaining for all three vessels was 5%.

Figure 4:
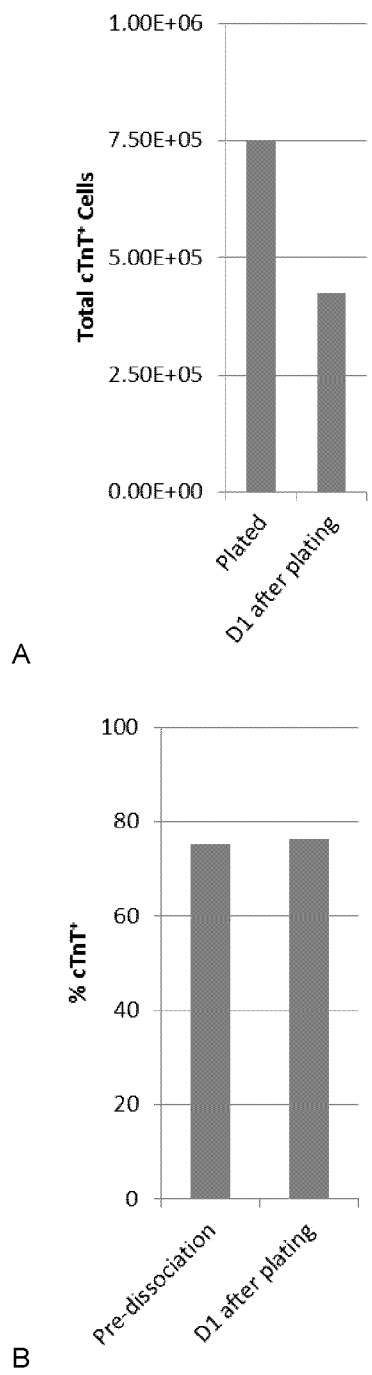
FIG. 4 depicts evaluation of cardiomyocytes produced and harvested according to one embodiment of the method provided herein; (A) shows that dissociation did not affect the attachment efficiency of $cTnT^+$ cells; (B) shows that expression of cardiac troponin T (cTnT), was maintained after dissociation.

Results:

After dissociation, the culture viability was 89.2% and only 2% of the culture remained as clusters of 5 or more cells. These results are similar to those observed with HES2 hPSC-derived cardiomyocytes which were manually dissociated (Viability: 86.9±4.1%, % clusters: 8±3%, n=10). Dissociation of the cardiomyocyte aggregates in the Mini-Bio 500 did not affect the attachment efficiency of $cTnT^+$ cells post-dissociation (FIG. 4A). Attachment efficiency (57%) was within the range observed with HES2 hPSC-derived cardiomyocyte aggregates (27-93%, n=3). The percentage of $cTnT^+$ cells in the culture remained consistent pre-dissociation (75.2%) and 1 day after plating (76.4%) (FIG. 4B). Contractile activity was observed in cultures from day 1 to day 7 after plating.

The method provided herein was successfully applied to harvest $3.2 \times 10^8$ hPSC-derived cardiomyocytes in the Mini-Bio 500. Cardiomyocytes were successfully plated and recovered after dissociation. Additionally, cardiomyocytes retained cTnT expression and contractile activity after dissociation and plating. The viability and percentage of cell clusters remaining post-dissociation in the STR were within the ranges observed in manual dissociation of a different cell line. Advantageously, 20 times more aggregates were processed in a single batch in the STR system, relative to manual dissociation. The method of cell dissociation in the STR system, relative to manual dissociation, required one-fifth of the time, only one dissociation step and reagent, and minimal operator interaction. As such, the presently disclosed cell dissociation protocol improves efficiency of the cardiomyocyte manufacturing process and enables culture on a scale of at least about 500 mL.

Figure 9:
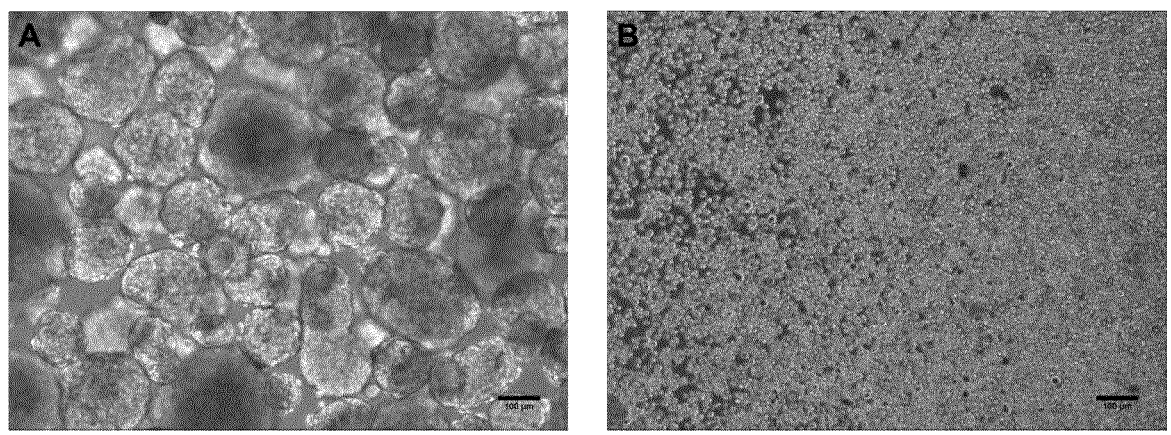
FIG. 9 depicts microscope images of cardiomyocyte aggregates, (A) prior to dissociation; and (B) following 3 hours of collagenase dissociation in the Ambr™15 (scale bars represent 100 μm).

Dissociation of PSC-derived cardiomyocytes using Collagenase in the Ambr™15 took 3 hours (FIG. 9). The final viable cell density was approximately $1.9 \times 10^6$ cells/mL, indicating there was a good yield of dissociated cells recovered following the 3 hour dissociation (approximately 120% of the estimated seeding density). The estimated starting density of cells was $1.6 \times 10^6$ cells/mL, but this value was based on a count of a small dissociated sample, thus a yield that is over the estimate of the sample count by 25% is not unusual.

Example 5

Varying Aggregate Sizes

Methods:

PSC Aggregate Expansion

Single cell adapted ESI-17 cells were inoculated into spinner flasks at a seeding density of 2.5E5 cells/mL with a total volume of 125 mL. For the first 24 hours, cells were cultured in mTeSR™1 medium (StemCELL Technologies) supplemented with 10 μM rho-kinase (ROCK) inhibitor Y-27632 (Tocris) at an agitation rate of 110 rpm. Following the first 24 hours, 50% medium exchanges of mTeSR™1 (without ROCK inhibitor) were performed daily using gentle centrifugation (200×g) to minimize loss of aggregates.

Small, medium and large PSC aggregates (with mean diameters of approximately 100, 175 and 210 μm, respectively) were harvested from spinner flasks on days 3, 6, and 8 for dissociation. A 2 mL sample of the spinner culture was taken on the day of dissociation and dissociated to single cells using TrypLE™ Select (Thermo Fisher) and counted to determine the viable cell density in the spinner flasks. A volume of aggregate suspension equivalent to $5.4 \times 10^7$ cells was removed from the spinner flask(s) and centrifuged at 200×g for 3 minutes. Aggregates were washed with 10 mL warm Dulbecco's PBS without calcium or magnesium ($PBS^{-/-}$, Thermo Fisher) supplemented with 10 μg/mL DNAse I (Calbiochem), centrifuging after the wash. Aggregates were then resuspended in a total volume of 12 mL warm $PBS^{-/-}$ supplemented with DNAse I as above.

Four mL of aggregate suspension was added to each of three Ambr™15 vessels. The vessels were loaded into the Ambr bioreactor, and cultured using the following settings: agitation rate=downstir 450 rpm, dissolved oxygen (DO)= 90%, temperature=37° C. Immediately after starting the bioreactor, 4 mL warm TrypLE™ Select supplemented with 10 μg/mL DNAse I was added to each vessel using the Ambr™15 liquid handler, resulting in a final cell concentration of $2.25 \times 10^6$ cells/mL.

Samples (200 μL) were removed from each vessel using the liquid handler every 5 minutes and transferred to a 24-well ultralow attachment plate (Corning) containing 400 μL DMEM/F12 (Thermo Fisher) supplemented with 10% fetal bovine serum (FBS, Thermo Fisher) and 10 μg/mL DNAse I. Images of the samples were captured using an inverted microscope and for samples that appeared to have only small cell clusters and single cells, a sample was measured for % viability, viable cell density (VCD) and aggregates using a NucleoCounter NC-200. Dissociation was considered to be complete when the average % aggregates remaining for all three vessels was 3%.

Figure 5:
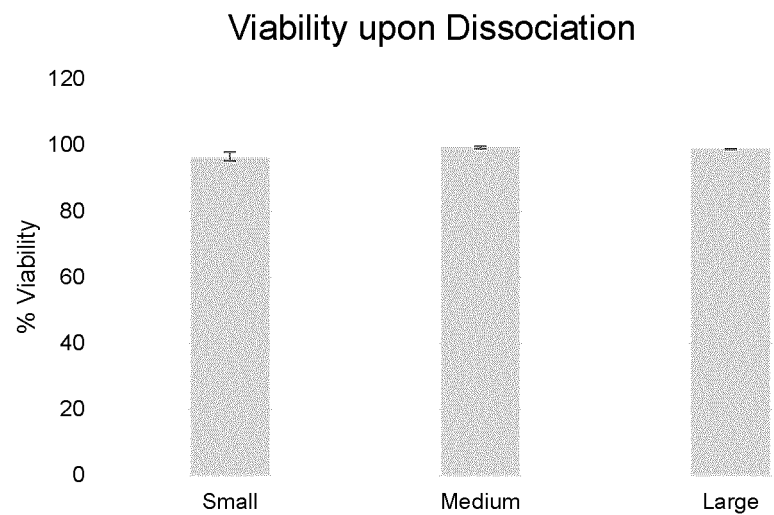
FIG. 5 depicts a bar chart illustrating percent viability of cultures following dissociation of small, medium, and large aggregates in the Ambr™15 bioreactor (N=3, data is shown as mean±SD).
Figure 6:
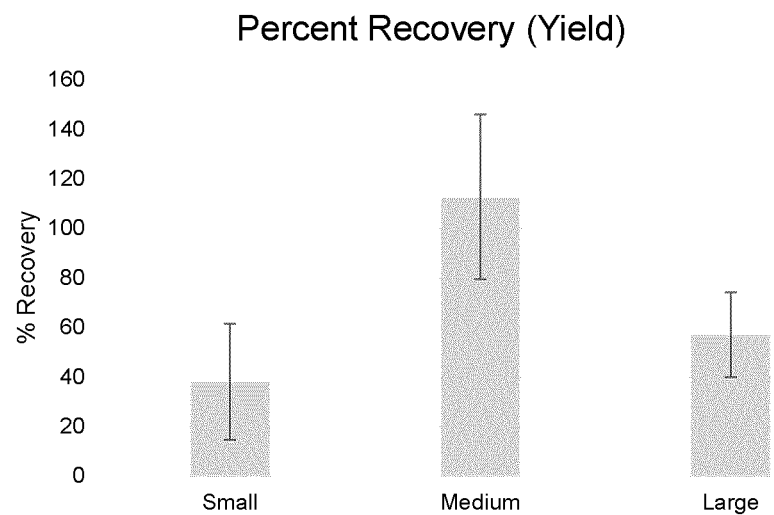
FIG. 6 depicts a bar chart illustrating percentage of cells remaining as viable cells at the time of dissociation in Ambr™15 vessels for different sized aggregates (N=3, data is shown as mean±SD).

Results:

Dissociation was achieved in the Ambr bioreactor using aggregates with mean diameters of 100, 175 and 220 μm. The time required for dissociation was highest for the large aggregates (55 minutes), whereas 40 minutes and 35 minutes were required for the small and medium aggregates, respectively. Viabilities of the cell suspensions at the time of dissociation were all high (>96%, FIG. 5). The percentage recovery of cells was lower than is typically achieved in larger-scale STRs for the small and large aggregates (FIG. 6). Recovery for the medium aggregates was very high (FIG.

6). There are a number of factors that may contribute to the lower recoveries for the small and large aggregates. First, the starting cell density was based on a small sample taken from the starting population, and that sample may not have been representative of the bulk cell suspension. Second, the geometry of the Ambr™15 vessels results in different mechanical shear forces than those that are seen in larger scale STRs, and this higher shear may result in higher cell loss from small aggregates where more of the cells in the aggregates are close to the surface. Third, for the large aggregates, a longer (by approximately 50%) dissociation time, combined with the presence of a large number of small aggregates within the population (the mean and median of the aggregate diameters were 220 and 216 μm respectively, the mode was 118 μm), may have been associated with reduced recovery.

The dissociation times required for all three aggregate sizes were longer than those achieved using larger volume STRs, where a typical dissociation time of approximately 9-11 minutes was achieved. This is likely due to the different vessel and impeller geometries and flow patterns of the small, rectangular vessels of the Ambr™15 bioreactor. The results in Table 4 demonstrate progression of dissociation of small aggregates over time. At 20 minutes, the percentage aggregates was 13%. An additional 20 minutes was required to bring the percent aggregates down below the 3% threshold.

TABLE 4

Time course of dissociation of small aggregates in the Ambr ™15 bioreactor showing the average % aggregates remaining at various time points.

| Time (mins) | % Aggregates |
|---|---|
| 20 | 13 |
| 25 | 9 |
| 30 | 6.3 |
| 35 | 5.7 |
| 40 | 3.0 |

Example 6

Varying Dissociation Force

Methods:

PSC aggregate expansion was carried out as in Example 5.

Medium aggregates, harvested from spinner flasks on day 6 were used to assess aggregate dissociation at various speeds. Methods were identical to those described in Example 5, except that the agitation rate for each set of three vessels was changed, so that cell cultures were dissociated one at a time at the following speeds (all downstir): 450 rpm, 650 rpm, 800 rpm, 1000 rpm and 1500 rpm.

Figure 7:
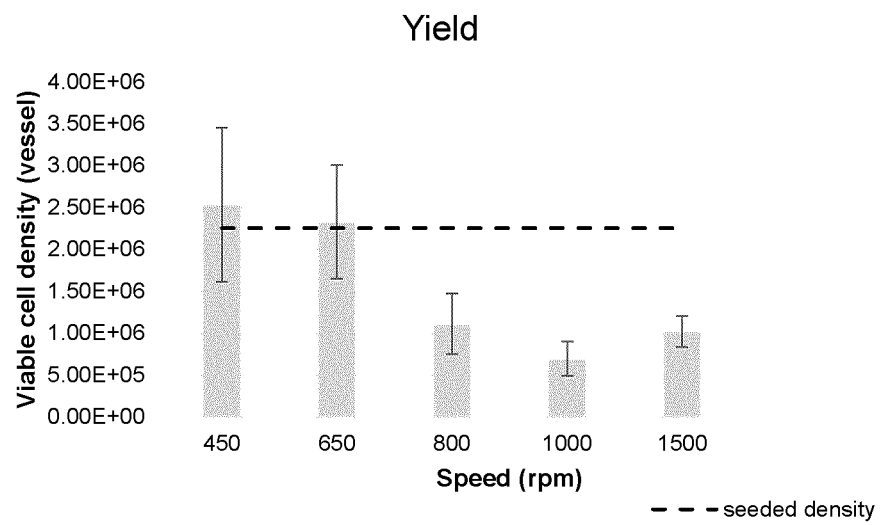
FIG. 7 depicts a bar chart illustrating percentage of cells remaining as viable cells at the time of dissociation in Ambr™15 vessels for medium aggregates at varying agitation rates (N=3, data is shown as mean±SD; the dotted line indicates the density of cells in the vessels at the start of the dissociation.

Results:

Dissociation time decreased as the agitation rate was increased and percent viability values for all speeds remained above 90% as measured using the nucleocounter (data not shown). At agitation rates above 650 rpm, significant loss of cell was observed (FIG. 7), indicating that high agitation rates were detrimental to cell yield. It is likely that cells were being sheared apart at 650 rpm, a speed that is significantly higher than typical culture agitation speed (450 rpm is standard for PSC culture in the Ambr™15).

Example 7

Varying Agitated Reactor Geometry

Methods:

PSCs were cultured as described in Example 5, in either spinner flasks (Bellco, 125 mL working volume), MiniBio500 STRs (Applikon, 125 mL working volume) or DASGIP™ Fermpro 200 mL STRs (Eppendorf, 125 mL working volume). Each of these vessels has a geometry that is distinct from the Ambr. After 5 days of culture, PSC aggregates were dissociated by washing aggregates with PBS$^{-/-}$, resuspending aggregates in 50% TrypLE™ Select and 50% PBS$^{-/-}$ supplemented with 10 μg/mL DNAse I at a cell density of 2.25×10$^6$ cells/mL, and returned to the STR in which the PSC aggregates had been cultured. For the MiniBio500 and DASGIP™ bioreactors, an agitation rate of 150 rpm was used, and temperature was controlled to 37° C. For the spinner flasks, an agitation rate of 100 rpm was used. Dissociations were performed for 9 minutes or until a majority of single cells were observed under a light microscope.

Figure 8:
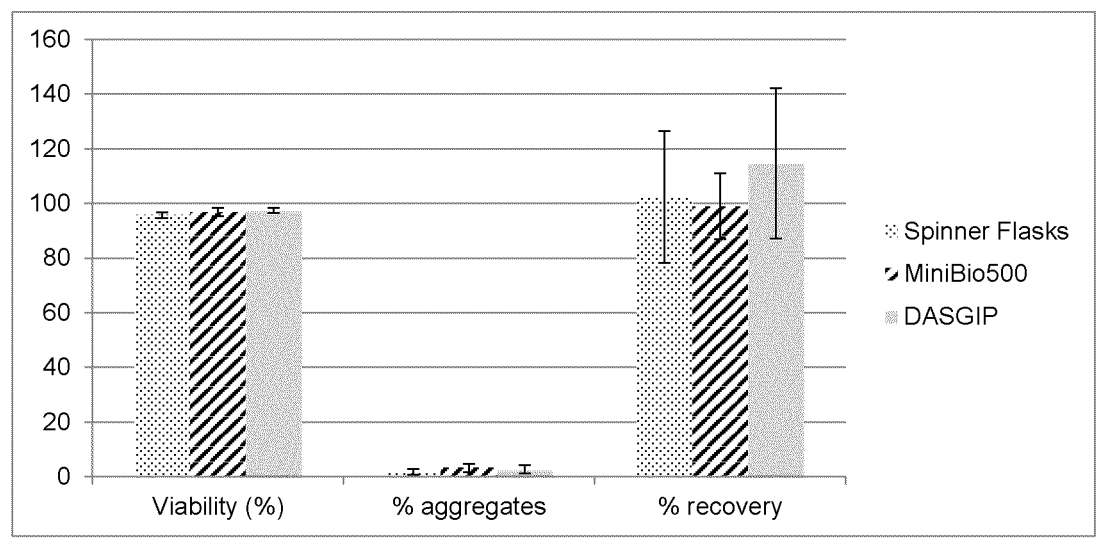
FIG. 8 depicts a bar chart illustrating cell viability, percent aggregates remaining, percent recovery, and time to dissociation for 50% TrypLE™ Select/50% PBS dissociations in three different styles of STRs. N=3, data is shown as mean±SD.

Results:

Agitation of PSC aggregates in a 50% TrypLE™/50% PBS mixture within larger scale STR cultures was sufficient to dissociate aggregates into mostly single cells, while maintaining high viability and cell recovery. PSCs expanded within spinner flasks, MiniBio500 STRs, and DASGIP™ STRs, were dissociated to single cells (<4% aggregates) in 9-11 minutes in the STR they were cultured in. Agitation during dissociation was equal to agitation during PSC culture for each type of STRs. Post-dissociation, cell viability was greater than 95% and the average recovery of cells after dissociation was >95% within each type of STR (FIG. 8, n=3 per STR, data is shown as mean±SD). The three STRs tested are unique in their geometries and together represent multiple designs, include paddle impellers (spinner flasks), cylindrical round bottom vessels (MiniBio500) and cylindrical flat bottom vessels (DASGIP™). The PSC dissociation method provided may be used in multiple types of STRs and aggregates may be dissociated within the vessels they were cultured in.

Although the invention has been described with reference to certain specific embodiments, various modifications thereof will be apparent to those skilled in the art without departing from the purpose and scope of the invention as outlined in the claims appended hereto. Any examples provided herein are included solely for the purpose of illustrating the invention and are not intended to limit the invention in any way. Any drawings provided herein are solely for the purpose of illustrating various aspects of the invention and are not intended to be drawn to scale or to limit the invention in any way. The disclosures of all prior art recited herein are incorporated herein by reference as if set forth in their entirety.

REFERENCES CITED

1. Fok and Zandstra, 2005 Stem Cells 23 1333-1342;
2. Cormier et al., 2006 Tissue Eng 12[11] 3233-3244;
3. zur Nieden et al 2007 J Biotechnol 129 421-432;
4. Hunt et al., 2014 Tissue Eng C 20[1] 76-89;
5. Krawetz et al., 2010 Tissue Eng C 16[4] 573-582;
6. Fluri et al., 2012 Nat Methods 9[5] 509-516;
7. Shafa et al., 2012 J Tissue Eng Regen Med 6 462-472;
8. Haraguchi et al., 2015 J Tissue Eng Regen Med 9 1363-1375;

9. Olmer et al., 2012 Tissue Eng C 18[10] 772-784;
10. Wang et al., 2013 Stem Cell Res 11 1103-1116;
11. Kallos and Behie, 1999 Biotechnol Bioeng 63[4] 473-483;
12. Gilbertson et al., 2006 Biotechnol Bioeng 94[4] 783-792;
13. Kempf et al., 2015 Nat Prot 10[9] 1345-1361;
14. Fryer and Laniauskas, US14/963730;
15. Papantoniou et al., 2011 Chem Eng Sci 66 57-581;
16. WO 2016/113369;
17. Davis et al., U.S. Ser. No. 14/956,408; and
18. Sart et al., 2014 Tissue Eng Part B Rev 20 365-380;

We claim:

1. A method for dissociating cell aggregates in an agitated reactor, the method comprising:
   providing a cell culture having a volume of at least about 500 mL comprising cell aggregates in the agitated reactor;
   contacting the cell aggregates with a dissociation reagent; and
   applying a dissociation force generated by the agitated reactor to the cell aggregates under conditions sufficient to dissociate the cell aggregates, comprising exposing the cell aggregates to the applied dissociation force for 4 hours or less.

2. The method of claim 1, wherein the contacting occurs:
   before or at substantially the same time as the applying of the dissociation force in the agitated reactor.

3. The method of claim 1, wherein the dissociation force is generated by movement of a stirrer, impeller, paddle, or wheel, by rocking, or by forced fluid flow entering the agitated reactor.

4. The method of claim 1, wherein the providing step comprises exposing the cell culture to a culture force in the agitated reactor and wherein the dissociation force is about 50% to 500% of the culture force.

5. The method of claim 1, further comprising:
   washing the cell culture prior to contacting the cell aggregates with the dissociation reagent;
   neutralizing and/or diluting the dissociation reagent; and/or
   washing the dissociated cells.

6. The method of claim 1, wherein the method is carried out in a closed system.

7. The method of claim 1, wherein the agitated reactor is a stirred tank reactor, wave-mixed/rocking reactor, up and down agitation reactor, spinner flask, shake flask, shaken bioreactor, paddle mixer, or vertical wheel bioreactor.

8. The method of claim 1, wherein the cell culture comprises a volume of about 500 mL-2,000 L.

9. The method of claim 1, wherein the cell culture comprises about $1 \times 10^6$ cells/mL to $1 \times 10^{15}$ cells/mL.

10. The method of claim 1, wherein the dissociated aggregates have a cell viability between about 50% and 100%.

11. The method of claim 1, wherein the dissociated aggregates comprise:
    aggregates that are at least 50% smaller than the provided cell aggregates; or
    substantially single cells.

12. The method of claim 1, wherein the provided cell aggregates have a diameter of about 150 microns to 800 microns.

13. The method of claim 1, wherein the cell aggregates substantially comprise:
    pluripotent stem cells;
    multipotent stem and/or progenitor cells; and/or
    somatic cells.

14. The method of claim 1, wherein the dissociation force generated comprises a Kolmogorov eddy size less than the size of the largest cell aggregate and greater than the diameter of a cell in the cell aggregates at Reynolds number >1000.

15. The method of claim 1, wherein the contacting occurs after the applying of the dissociation force in the agitated reactor.

16. The method of claim 1, wherein the providing step comprises exposing the cell culture to a culture force in the agitated reactor and wherein the dissociation force is about 100% of the culture force.

17. The method of claim 1, wherein the cell culture comprises a volume of between about 1 L to 1,000 L.

18. The method of claim 1, wherein the dissociated aggregates have a cell viability greater than 80%.

19. The method of claim 1, wherein the provided cell aggregates have a diameter of about 200 microns to 400 microns.

20. The method of claim 1, wherein the agitated reactor is a stirred tank reactor.

21. The method of claim 1, wherein the cell aggregates are exposed to the applied dissociation force for about 10 minutes.

22. A method for passaging cells, the method comprising:
    providing a cell culture having a volume of at least about 500 mL comprising cell aggregates in a first agitated reactor;
    contacting the cell aggregates with a dissociation reagent;
    applying a dissociation force generated by the agitated reactor to the cell aggregates under conditions sufficient to dissociate the cell aggregates, comprising exposing the cell aggregates to the applied dissociation force for 4 hours or less; and
    culturing at least a portion of the dissociated cell aggregates, thereby passaging the cells.

23. The method of claim 22, wherein the portion of the dissociated aggregates is cultured in the first agitated reactor.

24. The method of claim 22, wherein the portion of the dissociated aggregates is cultured in a second agitated reactor.

25. The method of claim 24, wherein the second agitated reactor is a different type of agitated reactor and/or is a different size than the first agitated reactor.

26. The method of claim 24, wherein the second agitated reactor is larger than the first agitated reactor.

27. A method for generating dissociated differentiated cells from a stem or progenitor cell population within an agitated reactor, the method comprising:
    providing a cell culture having a volume of at least about 500 mL comprising a population of stem and/or progenitor cells in the agitated reactor;
    differentiating the stem and/or progenitor cells into differentiated cell aggregates within the agitated reactor under conditions suitable for differentiation;
    contacting the differentiated cell aggregates with a dissociation reagent; and
    applying a dissociation force generated by the agitated reactor to the cell aggregates under conditions sufficient to dissociate the differentiated cell aggregates, comprising exposing the cell aggregates to the applied dissociation force for 4 hours or less.

* * * * *

UNITED STATES PATENT AND TRADEMARK OFFICE
CERTIFICATE OF CORRECTION

PATENT NO. : 11,242,503 B2
APPLICATION NO. : 16/072379
DATED : February 8, 2022
INVENTOR(S) : Nicholas Timmins et al.

Page 1 of 1

It is certified that error appears in the above-identified patent and that said Letters Patent is hereby corrected as shown below:

In the Specification

Column 23, Lines 26-27, "was 5%" should be --was $\leq$ 5%--.

Column 24, Lines 53-54, "and aggregates" should be --and % aggregates--.

Column 24, Line 56, "was 3%" should be --was $\leq$ 3%--.

Signed and Sealed this
Twenty-ninth Day of March, 2022

Drew Hirshfeld
*Performing the Functions and Duties of the*
*Under Secretary of Commerce for Intellectual Property and*
*Director of the United States Patent and Trademark Office*